(12) United States Patent
Cense et al.

(10) Patent No.: US 6,976,984 B2
(45) Date of Patent: *Dec. 20, 2005

(54) SKIN TREATING DEVICE COMPRISING A PROTECTED RADIATION EXIT OPENING

(75) Inventors: Abraham Josephus Cense, Cambridge, MA (US); Jan Simonsen, Struer (DK); Michiel Errit Roersma, Eindhoven (NL); Lucas Josef Maria Schlangen, Eindhoven (NL); Antonius Maarten Nuijs, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 300 days.

This patent is subject to a terminal disclaimer.

(21) Appl. No.: 10/109,774

(22) Filed: Mar. 29, 2002

(65) Prior Publication Data

US 2002/0173781 A1  Nov. 21, 2002

(30) Foreign Application Priority Data

Mar. 30, 2001  (EP) ................................. 01201191

(51) Int. Cl.[7] ............................................. A61B 18/18
(52) U.S. Cl. ............................... 606/9; 606/10; 606/12
(58) Field of Search .......................... 606/8–13, 16–19

(56) References Cited

U.S. PATENT DOCUMENTS

| | | | | |
|---|---|---|---|---|
| 4,950,267 A | * | 8/1990 | Ishihara et al. | 606/12 |
| 5,501,680 A | * | 3/1996 | Kurtz et al. | 606/9 |
| 5,540,677 A | * | 7/1996 | Sinofsky | 606/8 |
| 5,653,706 A | * | 8/1997 | Zavislan et al. | 606/9 |
| 6,074,382 A | * | 6/2000 | Asah et al. | 606/9 |
| 6,533,774 B1 | * | 3/2003 | Ota | 606/9 |
| 6,706,035 B2 | * | 3/2004 | Cense et al. | 606/9 |

FOREIGN PATENT DOCUMENTS

| | | | |
|---|---|---|---|
| EP | 0885629 A2 | 12/1998 | A61N 5/06 |
| EP | 1057454 A2 | 5/2000 | A61B 18/20 |
| WO | WO9807379 | 8/1997 | A61B 17/41 |
| WO | WO0126573 | 9/2000 | A61B 18/20 |
| WO | WO0062700 | 10/2000 | A61B 18/20 |

OTHER PUBLICATIONS

Patent Abstract of Japan: Publication No. JP5057026, Application No. JP19910221400, Publication Date: Mar. 9, 1993, Int'l Class A61N5/06.

* cited by examiner

*Primary Examiner*—A. Farah

(57) ABSTRACT

A device treats skin by radiation. The device has a housing accommodating a radiation source and having an exit opening for the radiation. The device activates the radiation source only if the presence of skin immediately in front of the exit opening is detected. The radiation source cannot be activated if the exit opening is not covered.

17 Claims, 3 Drawing Sheets

SKIN TREATING DEVICE COMPRISING A PROTECTED RADIATION EXIT OPENING

Figure 1:
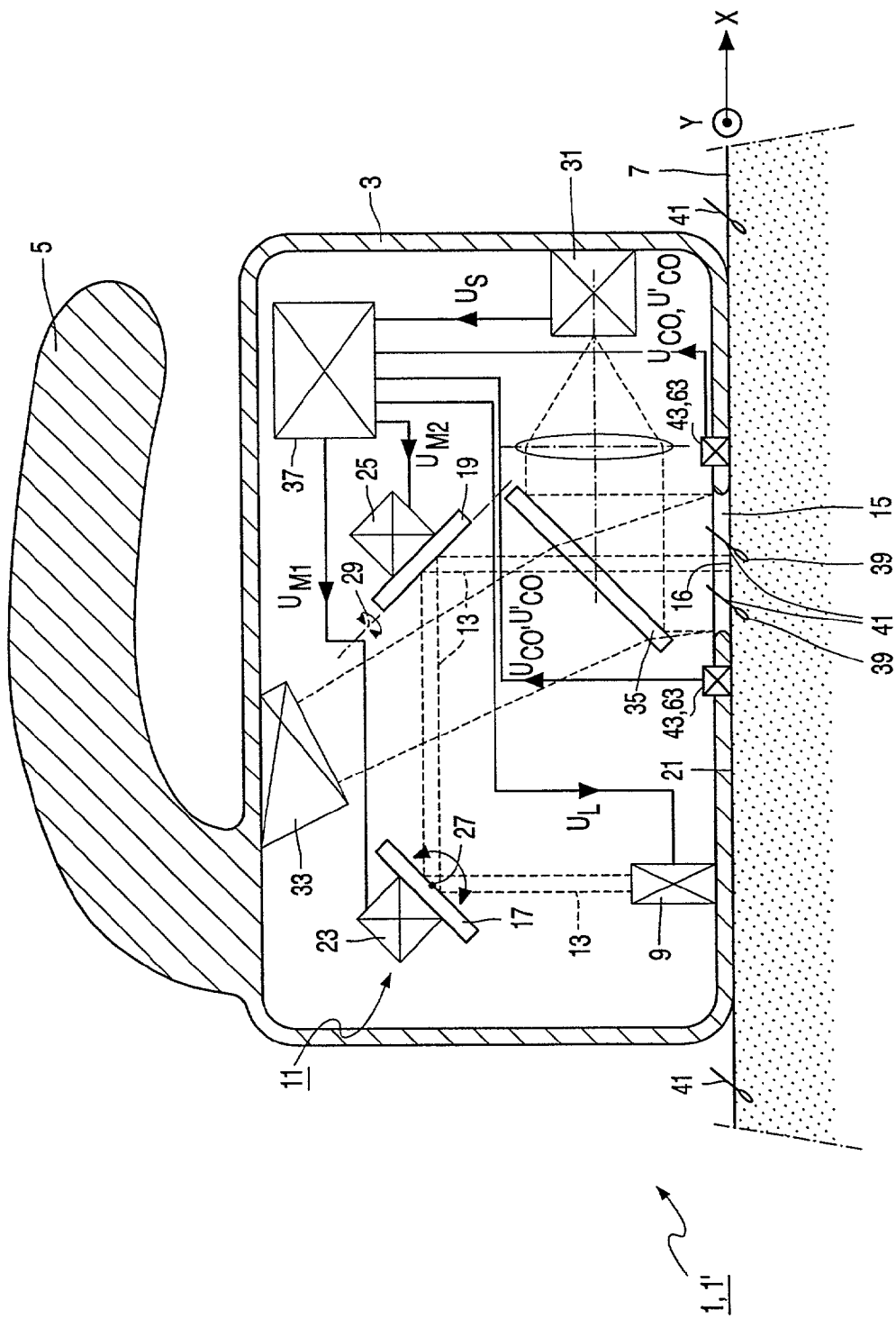

The invention relates to a device for treating skin by means of radiation, which device comprises a housing, which accommodates a radiation source and which is provided with an exit opening for the radiation, a detector for detecting the presence of skin directly in front of the exit opening, and a control unit which activates the radiation source only if the detector detects the presence of skin directly in front of the exit opening.

A device of the type mentioned in the opening paragraph is known from JP-A-5-57026. The known device is a device for the medical treatment of skin by means of laser light. The device is used, for example, for treating birthmarks, such as naevus pigmentosus and naevus vinosus, present on the skin, psoriasis, or aberrations of blood vessels present in the skin. In the housing of the device two laser sources are arranged which, in operation, each generate a laser beam. The laser beams are obliquely oriented with respect to the exit opening. If the housing is correctly placed on the skin, i.e. if the skin is present directly in front of the exit opening and hence the exit opening is completely covered and enclosed, the obliquely oriented laser beams are reflected by the skin and said reflected laser beams are incident on two photosensors that are also arranged in the housing. If the skin is not present directly in front of the exit opening, for example if the device is obliquely positioned on the skin or at some distance from the skin, the reflected laser beams do not, or only partly, impinge on the two photosensors. In this state, the control unit co-operating with the photosensors deactivates the two laser sources. In this manner, emission of the laser beams via the exit opening is impeded if the exit opening is not fully covered and enclosed, so that accidentally or deliberately harming or injuring someone by means of the laser beams is impeded substantially.

A drawback of the known device resides in that it is not optimally protected against accidental or deliberate emission of laser beams via the exit opening. For example, the protection is sub-optimal if the exit opening is covered with a glass plate, since the laser beams are partly reflected by the glass plate, so that the laser beams are still incident on the photosensors. The laser beams are not deactivated either if the exit opening is covered with another material that partly reflects the laser beams, as a result of which there may be a fire risk. Due to said drawback, the device is less suitable for the consumer market.

It is an object of the invention to provide a device of the type mentioned in the opening paragraph, the radiation source of which can be activated only if the medium present directly in front of the exit opening actually is human skin, so that optimum protection against accidental or deliberate emission of radiation via the exit opening is achieved and the device is more suited for the consumer market.

To achieve this object, a device of the type mentioned in the opening paragraph is characterized in accordance with the invention in that the detector can suitably be used to measure a biophysical property by means of which the skin can be characterized, the control unit comprising a comparator for comparing a value or condition of the property, measured by means of said detector, with a skin-characteristic value or condition of the property. In the device in accordance with the invention, the radiation source is activated or deactivated by the control unit on the basis of the comparison made by the comparator. The radiation source is activated by the control unit only if the value or condition of said biophysical property, measured by the detector, corresponds, within predetermined limits, to the human skin-characteristic value or condition of said property. By using a biophysical property enabling the skin to be characterized in a substantially unique way, a very reliable protection of the device against accidental or deliberate emission of the radiation via the exit opening is achieved, and the radiation source can be activated only if the medium present directly in front of the exit opening actually is human skin. By virtue thereof, the device can particularly suitably be used for the consumer market.

A particular embodiment of a device in accordance with the invention is characterized in that the housing comprises a skin contact element in which the exit opening is formed and in which said detector is provided near the exit opening. As the detector is provided in said skin contact element, the control unit activates the radiation source only if the detector detects the presence of human skin against the skin contact element. By virtue thereof, it is more effectively prevented that the radiation source is activated if the skin contact element does not contact the skin, in particular if there is still a small opening between the skin contact element and the skin. The reliability of the device is further improved thereby. Preferably, the device comprises at least two detectors which are arranged at some distance from each other near the exit opening, for example on either side of the exit opening. In this manner, it is more effectively prevented that the radiation source can be activated if the exit opening is only partly covered.

A further embodiment of a device in accordance with the invention is characterized in that a series of detectors is provided in the skin contact element around the exit opening to measure the biophysical property. In this embodiment, the control unit activates the radiation source only if all detectors present in the skin contact element measure a skin-characteristic value or condition of the biophysical property and hence detect the presence of human skin against the skin contact element. The detectors are arranged at small regular distances from each other, so that it is precluded, in a substantially optimum manner, that the radiation source can be activated if the exit opening is only partly covered, resulting in a substantially optimum reliability of the device.

Yet another embodiment of a device in accordance with the invention is characterized in that the detector can suitably be used to measure a scattering coefficient and/or an absorption coefficient of the skin for light of a predetermined wavelength. Due to the presence of blood, water, cells, keratin and melanin in human skin, light is absorbed and scattered in the human skin in a very characteristic way as a function of the wavelength of the light. By measuring the scattering coefficient and/or the absorption coefficient for light having a predetermined wavelength by means of said detector, it is very reliably determined whether the medium that covers the exit opening is human skin.

A particular embodiment of a device in accordance with the invention is characterized in that the detector is provided with a light sensor and a light source for light of said predetermined wavelength, which light source is arranged next to the light sensor and optically separated from said light sensor, the light source and the light sensor being in contact with the skin only if the skin contact element is in contact with the skin, and the detector determining the scattering coefficient and/or absorption coefficient by comparing an amount of light measured by the light sensor with an amount of light generated by the light source. As the light source is optically separated from the light sensor, the light originating from the light source cannot directly reach the light sensor. The light from the light source is capable of reaching the light sensor through scattering in the skin. In order to achieve that a substantial portion of the light from the light source reaches the light sensor through scattering in the skin, it is necessary that both the light source and the light sensor, and hence also the skin contact element, are in contact with the skin. Insufficient or no contact between the skin and the light source and/or the light sensor leads to a substantial reduction of the amount of light reaching the light sensor. Thus, by means of the detector, the value of the scattering coefficient and/or absorption coefficient is reliably determined and, in addition, it is reliably detected whether the skin actually contacts the skin contact element.

A further embodiment of a device in accordance with the invention is characterized in that the detector is provided with a further light source for light of a further, predetermined wavelength, which light source is also arranged next to the light sensor, optically separated from said light sensor and in contact with the skin only if the skin contact element is in contact with the skin, the detector determining the scattering coefficient and/or absorption coefficient for both wavelengths by comparing the amounts of light measured by the light sensor with the amounts of light generated by the two light sources. In this further embodiment, the detector determines the scattering coefficient and/or the absorption coefficient for two different wavelengths of the light. As a still better characterization of the human skin is achieved by the values of the scattering coefficient and/or absorption coefficient for two different wavelengths of the light, the reliability of the device is still further improved. In this embodiment use is made of only one light sensor, the light sources, for example, alternately generating a light pulse, so that the structure of the detector is comparatively simple.

A still further embodiment of a device in accordance with the invention is characterized in that the light source and the further light source are arranged on one side of the light sensor. By virtue thereof, the light from the two light sources reaches the light sensor by scattering of the light in the same part of the skin, as a result of which the accuracy of the detector is improved.

A particular embodiment of a device in accordance with the invention is characterized in that the light source is a LED, and the light sensor is a photodiode. Said LED and photodiode are comparatively inexpensive and have small dimensions, so that the price and the dimensions of the detector are limited.

A further embodiment of a device in accordance with the invention is characterized in that the detector can suitably be used to measure a reflection coefficient of the skin for light of a predetermined wavelength. Due to the presence of blood, water, cells, keratin and melanin in human skin, light is reflected very characteristically by the human skin as a function of the wavelength of the light. By measuring the reflection coefficient for light of a predetermined wavelength by means of the detector, it is reliably established whether the medium, that is present directly in front of the exit opening, is human skin.

A still further embodiment of a device in accordance with the invention is characterized in that the detector is provided with a light sensor and a light source for light of said predetermined wavelength, which light source is arranged next to the light sensor and optically separated from said light sensor, the light source and the light sensor being situated at a predetermined distance from the skin only if the skin contact element is in contact with the skin, and the detector determining the reflection coefficient by comparing an amount of light measured by the light sensor with an amount of light generated by the light source. As the light source is optically separated from the light sensor, the light from the light source cannot reach the light sensor directly. The light from the light source can reach the light sensor by reflection via the surface of the skin. The amount of light reaching the light sensor depends on the reflection coefficient and on the distance from the light source and the light sensor to the skin. In order to make sure that a predetermined amount of light from the light source reaches the light sensor by reflection, it is necessary, on the one hand, that the light is actually reflected by skin, i.e. the exit opening must actually be covered by skin, and on the other hand, said predetermined distance between the skin and the light source, and between the skin and the light sensor must actually exist, i.e. the skin contact element must be in contact with the skin. In this manner, using the detector, it is reliably detected, on the one hand, whether the medium present directly in front of the exit opening is human skin and, on the other hand, whether the skin actually is in contact with the skin contact element and the exit opening is fully covered and enclosed by the skin.

A particular embodiment of a device in accordance with the invention is characterized in that the device is a hair removing device, wherein the radiation source comprises a laser source, and the device is further provided with an adjustable laser beam manipulator for positioning a laser beam supplied, in operation, by the laser source in a target position on the skin to be treated. In such an embodiment of the device in accordance with the invention, the invention becomes effectual in a particular way because the laser beam generated by the laser source has a comparatively high light intensity and hence, in the event of accidental or deliberate emission via the exit opening, is capable of causing substantial damage or inflict serious injuries, particularly, to the eyes.

A further embodiment of a device in accordance with the invention is characterized in that the device is a hair removing device, wherein the radiation source comprises a flash light for generating light pulses, and the device is further provided with a directing element for directing the light pulses to the exit opening. In such an embodiment of the device in accordance with the invention, the invention also becomes effectual in a particular way because the light pulses generated by the flash light have a comparatively high light intensity and hence, in the event of accidental or deliberate emission via the exit opening, are capable of causing substantial damage or inflict serious injuries, in particular, to the eyes.

Figure 2:
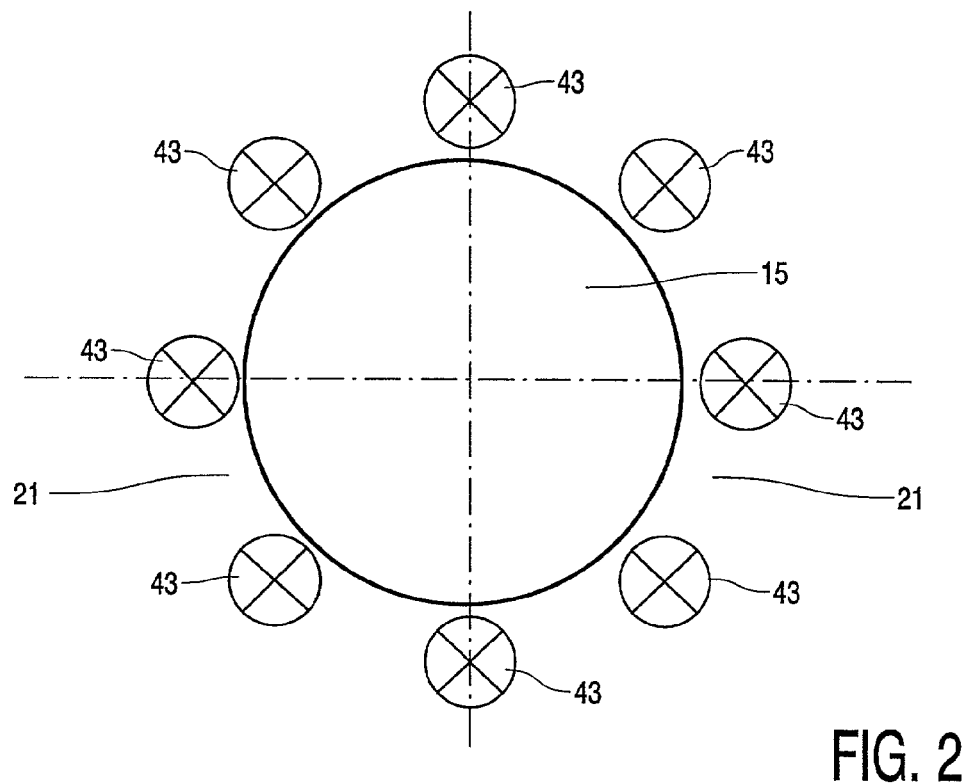
Figure 3:
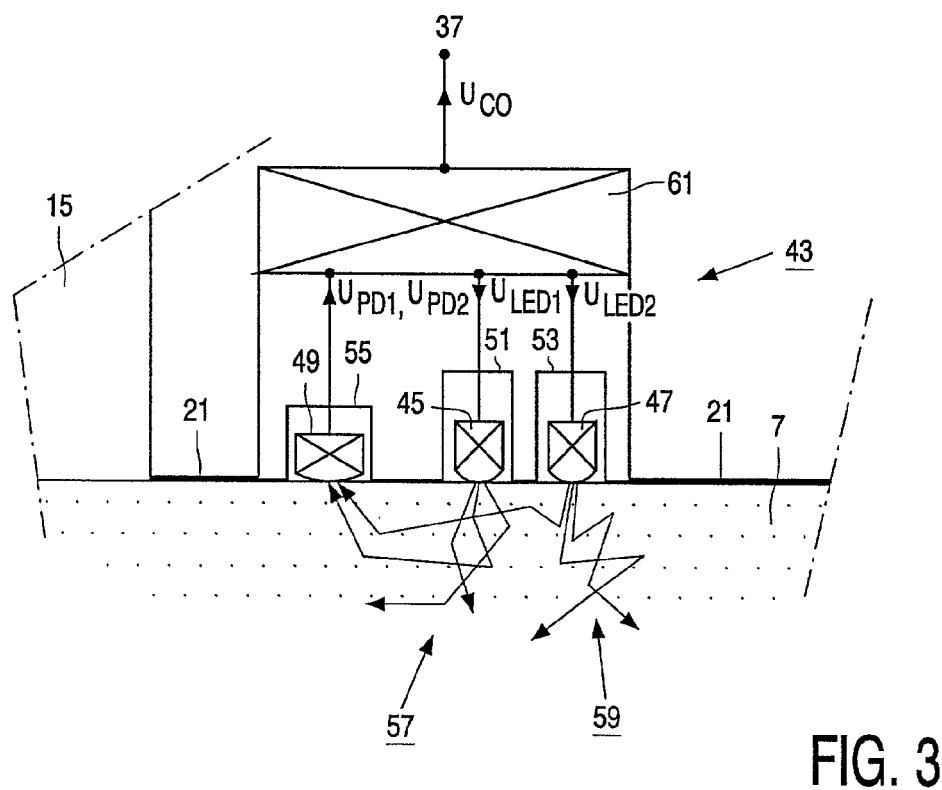
Figure 4:
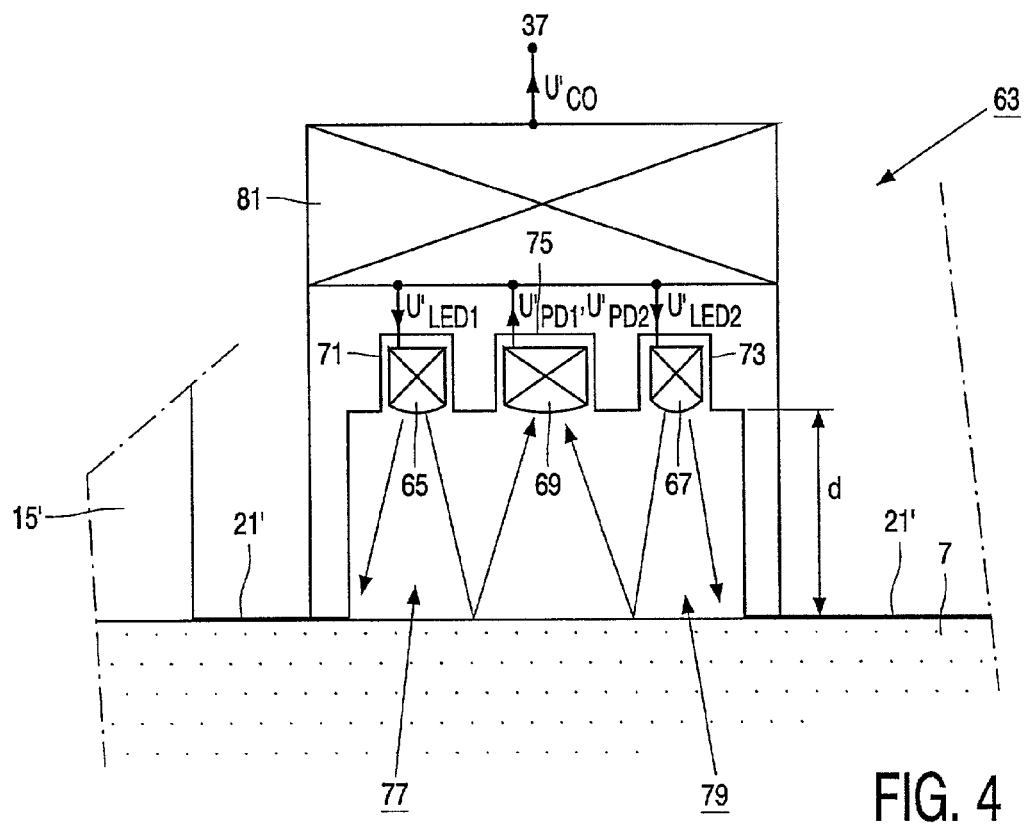
Figure 5:
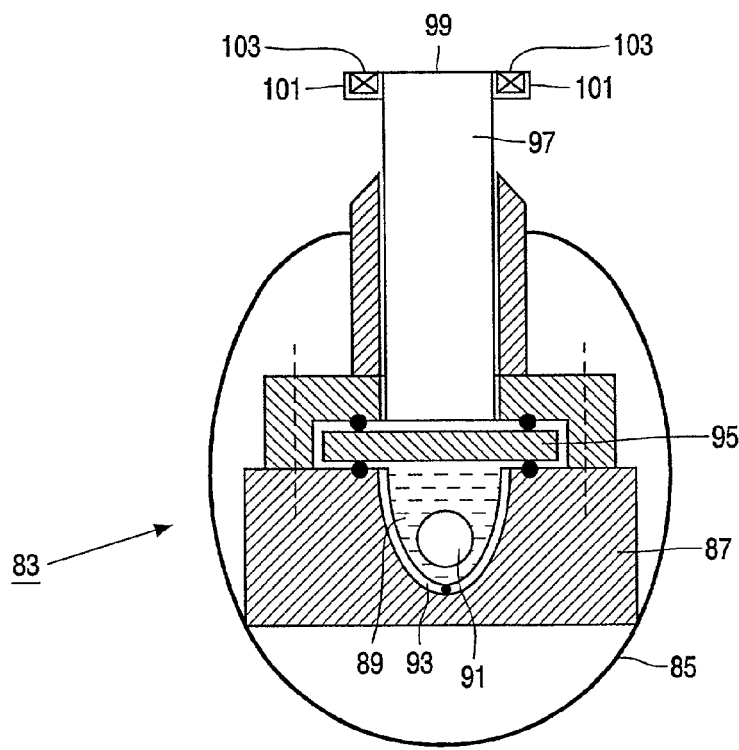

In the following, embodiments of the device in accordance with the invention are explained in detail with reference to the figures, in which:

FIG. 1 diagrammatically shows a first example of a device in accordance with the invention, FIG. 2 diagrammatically shows an exit opening with a series of detectors of the device in accordance with FIG. 1, FIG. 3 diagrammatically shows one of the detectors in accordance with FIG. 2, FIG. 4 diagrammatically shows a detector of a second example of a device in accordance with the invention, and FIG. 5 diagrammatically shows a third example of a device in accordance with the invention.

FIG. 1 diagrammatically shows a first example of a device 1 in accordance with the invention for treating skin by means of radiation, said device being a hair removing device, in particular a laser epilation device, by means of which hairs present on the skin are removed for a comparatively long period of time or permanently by means of laser light. Said device 1 comprises a housing 3 with a handle 5, so that the device 1 is portable and can be placed on or moved over skin 7 to be treated. The housing 3 accommodates a radiation source, in particular a laser source 9 such as a diode laser, and an adjustable laser beam manipulator 11 by means of which a laser beam 13 generated, in operation, by the laser source 9 can be positioned, via an exit opening 15 provided in the housing 3, on the skin 7 in an target position 16. In the example shown, the laser beam manipulator 11 comprises a first adjustable tilting mirror 17 and a second adjustable tilting mirror 19, which are both arranged at an angle of approximately 45° with respect to a flat skin contact element 21, in which the exit opening 15 is situated and which, in the example shown, forms a bottom wall of the housing 3. By means of a first actuator 23 and a second actuator 25, the tilting mirrors 17 and 19, respectively, can be tilted about, respectively, a first tilt axis 27, which extends in the plane of the first tilting mirror 17 and is directed substantially parallel to the second skin contact element 21, and a second tilt axis 29, which extends in the plane of the second tilting mirror 19 and intersects the first tilt axis 27 substantially perpendicularly. By tilting the two tilting mirrors 17 and 19, the target position 16 of the laser beam 13 can be displaced over the skin 7 in a direction parallel to an X-direction and a Y-direction extending perpendicularly thereto, both directions being parallel to the skin contact element 21.

To determine successive target positions, the device 1 is provided, in the example shown, with an image sensor 31, such as a CCD image sensor or CMOS image sensor, which records an image of the part of the skin 7 that is situated directly in front of the exit opening 15, by means of an auxiliary lamp 33 and a transparent mirror 35. The device 1 further comprises a control unit 37 to which the image sensor 31 supplies an electrical signal $u_S$ which corresponds to the image recorded by the image sensor 31. The control unit 37 comprises a sensor by means of which, on the basis of the image recorded, the positions of the hair roots 39 of the hairs 41 present on said part of the skin 7 are determined on said part of the skin 7. The control unit 37 controls the two actuators 23 and 25 by means of, respectively, an electrical signal $u_{M1}$ and an electrical signal $u_{M2}$, in such a manner that the laser beam 13 is successively positioned in a series of target positions that correspond to the positions of the hair roots 39 thus determined. In each target position 16, the laser beam 9 is activated, during a predetermined period of time and with a predetermined intensity, by the control unit 37 by means of an electrical signal $u_L$, so that the hair roots 39 present are successively heated and die. For a detailed explanation of the operation of the device 1, which is only briefly described herein, reference is made to WO-A-00/62700.

The laser beam 13 generated by the laser source 9 has a comparatively high intensity and hence is harmful when it contacts, for example, the eye. The device 1 in accordance with the invention is provided with means that can be used to prevent, to the extent possible, that the laser source 9 can be activated if the exit opening 15 is not, or not completely, covered and enclosed by human skin, or if the exit opening 15 is covered with a medium other than human skin, such as glass. The reliability of said means is very high, so that the device 1 in accordance with the invention can particularly suitably be employed in the consumer market by inexperienced persons that are not skilled in the art. As shown in FIG. 1 and FIG. 2, said means comprise a series of detectors 43 which are provided in the skin contact element 21 near the exit opening 15. In the example shown, said means comprise eight detectors 43 which are arranged at small, regular distances from each other around the exit opening 15. The detectors 43 can suitably be used to measure a biophysical property by means of which the human skin can be characterized. In the example shown, said biophysical property is the scattering coefficient and/or the absorption coefficient of the skin 7 for light of a predetermined wavelength. As shown in FIG. 3, the detectors 43 of the example shown each comprise two light sources 45, 47 for light having two different, predetermined wavelengths, in the example shown two LEDs, and a single light sensor 49, in the example shown a photosensor, which is arranged next to the light sources 45, 47. The light sources 45, 47 and the light sensor 49 are each arranged in a separate chamber 51, 53, 55 of the detector 43, as a result of which the light sensor 49 is optically separated from the light sources 45, 47, i.e. light from the light sources 45, 47 cannot directly reach the light sensor 49. As shown in FIG. 3, light beams 57, 59 from the light sources 45, 47, on the other hand, are capable of reaching the light sensor 49 through scattering in the skin 7. To make sure that a substantial part of the light beams 57, 59 from the light sources 45, 47 can reach the light sensor 49, the light sources 45, 47 and the light sensor 49 must be in direct contact with the skin 7. The detector 43 further comprises an electrical circuit 61 that successively activates both light sources 45, 47 for a short period of time by means of two electrical signals $u_{LED1}$ and $u_{LED2}$. As a result, the circuit 61 receives two successive electrical signals $u_{PD1}$ and $u_{PD2}$ from the light sensor 49 which correspond to the amounts of light that the light sensor receives through scattering in the skin 7 from, respectively, the two light sources 45 and 47. The circuit 61 subsequently determines the values of the scattering coefficient and/or the absorption coefficient of the skin 7 for the two different wavelengths of the two light sources 45, 47 by comparing the amounts of light received with the amounts of light generated by the light sources 45, 47, which amounts of light are determined by the signals $u_{LED1}$ and $u_{LED2}$. The circuit 61 converts the values of the scattering coefficient and/or absorption coefficient thus measured into an electrical signal $u_{CO}$. As shown in FIG. 1, the electrical signals $u_{CO}$ of all detectors 43 are received by the control unit 37 of the device 1. The control unit 37 comprises a comparator, not shown in the Figures, which compares the measured values of the scattering coefficient and/or absorption coefficient with values for the scattering coefficient and/or absorption coefficient that are characteristic of human skin and that are stored in a memory of the control unit 37. The control unit 37 can only activate the laser source 9 if the values measured by all detectors 43 correspond, within predetermined limits, to human skin-characteristic values, i.e. if all detectors 43 detect the presence of human skin. As shown in FIG. 3, the light sources 45, 47 and the light sensor 49 are arranged in the chambers 51, 53, 55, respectively, in such a manner that the light sources 45, 47 and the light sensor 49 only contact the skin 7 if the skin contact element 21 contacts the skin 7 at the location of the relevant detector 43, i.e. if there is no opening between the skin contact element 21 and the skin 7. In this manner it is achieved that the detectors 43 can also detect whether the skin contact element 21 fully contacts the skin 7. If, at the location of one of the detectors 43, the skin contact element 21 is not in contact with the skin 7, then the light sources 45, 47 and/or the light sensor 49 of the relevant detector 43 are not in contact with the skin, as a result of which the amounts of light originating from the light sources 45, 47 and reaching the light sensor 49 are substantially reduced and the values of the scattering coefficient and/or absorption coefficient measured by the light sensor do not correspond, within the predetermined limits, with the human skin-characteristic values. As the control unit 37 can only activate the laser source 9 if all detectors 43 detect the presence of human skin against the skin contact element 21, a very reliable protection of the device 1 is provided against accidental or deliberate emission of the laser beam 13 via the exit opening 15. As a series of detectors 43 is used around the exit opening 15, the laser source 9 can only be activated if the exit opening 15 is completely covered. If the exit opening 15 is only partly covered, at least one of the detectors 43 does not detect the skin 7, as a result of which the laser source 9 cannot be activated. The laser source 9 cannot be activated either if the device 1 is obliquely arranged on the skin 7 or at a short distance from the skin 7, because, in this case, at least one of the detectors 43 is not in contact with the skin 7. The laser source 9 cannot be activated either if the medium present in front of the exit opening 15 is not human skin. In human skin, light is scattered and absorbed in a very characteristic way as a function of the wavelength of the light, which can be attributed to the presence of various components such as blood, water, cells, keratin and melanin. By means of the detectors 43, the values of the scattering coefficient and/or absorption coefficient are measured for two different wavelengths of the light, green light in the example shown, which has a comparatively short wavelength, and red light, which has a comparatively long wavelength. The combination of the values of these coefficients for said two types of light is very specific in human skin, so that this enables human skin to be characterized in a substantially unique way and the detectors 43 can detect the presence of human skin against the skin contact element 21 with a very high degree of certainty. If the exit opening 15 is covered with a different medium, such as glass, transparent synthetic resin or paper, the detectors 21 detect different values of these coefficients, so that the control unit 37 cannot activate the laser source 9.

It is to be noted that instead of eight detectors 43, a different number of detectors can be applied in the device 1. A reasonable degree of protection is already achieved if only one detector 43 is provided in the skin contact element 21 near the exit opening 15. Preferably, however, the device comprises at least two detectors 43 which are arranged at some distance from each other near the exit opening 15, for example on either side of the exit opening 15, so that also a reasonable degree of protection is achieved in situations where the exit opening 15 is covered only partly. It is further noted that instead of the detectors 43, it is alternatively possible to use detectors by means of which the scattering coefficient and/or absorption coefficient for only one value of the wavelength of the light is measured. As light is scattered and absorbed in a very characteristic way in the human skin as a function of the wavelength, a very reliable detection can already be achieved by carrying out a measurement at only one predetermined wavelength. The invention also comprises embodiments, however, in which the detectors carry out measurements for three or more values of the wavelength. It is further noted that the structure of the detectors 43 is simple, which can be attributed to the fact that the light sensor 49 is used for both light sources 45, 47. The invention also comprises embodiments, however, wherein a separate light sensor is used for each light source 45, 47, which light sensor, for example, is sensitive only to light of the wavelength of the associated light source. It is further noted that the two light sources 45, 47 in the detector 43 are arranged on one side of the light sensor 49. This has the advantage that the light from the two light sources 45, 47 reaches the light sensor 49 by scattering of the light in the same part of the skin 7, so that the accuracy of the detector 43 is improved. Acceptable results are also achieved, however, in an alternative embodiment of the device in accordance with the invention, wherein the light sources 45, 47 are arranged on both sides of the light sensor 49. The LEDs and photosensors employed in the detectors 43 are comparatively inexpensive and have small dimensions, so that the cost price and the dimensions of the detectors 43 are limited. The invention also comprises embodiments wherein a different type of light source and/or a different type of light sensor is employed in the detectors 43. It is further noted that the invention also includes embodiments wherein, unlike the example shown in FIG. 3, the circuits 61 do not form part of the detectors 43 but of the control unit 37.

As shown in FIG. 1, a second example of a device 1' in accordance with the invention is substantially identical to the above-described device 1 in accordance with the first example. The device 1' differs mainly from the device 1 in that the device 1' is provided with eight detectors 63, instead of eight detectors 43, which detectors 63 can suitably be used to measure a reflection coefficient of the skin 7 with respect to light of a predetermined wavelength. Therefore, in the following description only the detectors 63 of the device 1' will be discussed, one of said detectors being diagrammatically shown in FIG. 4. As shown in FIG. 4, the detectors 63 each comprise, in the example shown, two light sources 65, 67 for generating light of two different, predetermined wavelengths. In the example shown said light sources are two LEDs. The detector 63 further comprises a single light sensor 69, i.e. a photosensor in the example shown, which is arranged between the two light sources 65, 67. The light sources 65, 67 and the light sensor 69 are each provided in a separate chamber 71, 73, 75, respectively, of the detector 63, as a result of which the light sensor 69 is optically separated from the light sources 65, 67. As shown in FIG. 4, light beams 77, 79 from the light sources 65, 67 can reach the light sensor 69 through reflection via the surface of the skin 7. The detector 63 further comprises an electrical circuit 81 which successively activates the two light sources 65, 67 for a short period of time by means of two electrical signals $u'_{LED1}$ and $u'_{LED2}$. As a result, the circuit 81 successively receives two electrical signals $u'_{PD1}$ and $u'_{PD2}$ from the light sensor 69, which electrical signals correspond to the amounts of light received by the light sensor 69 from, respectively, the two light sources 65 and 67 through reflection via the skin 7. The circuit 81 subsequently determines the values of the reflection coefficient of the skin 7 with respect to the two different wavelengths of the light sources 65 and 67 by comparing the amounts of light received with the amounts of light generated by the light sources 65, 67, which amounts of light are determined by the signals $u'_{LED1}$ and $u'_{LED2}$. The circuit 81 converts the values of the reflection coefficient thus measured into an electrical signal $u'_{CO}$ which, as shown in FIG. 1, is received by the control unit 37 of the device 1'. The control unit 37, which compares the measured values of the reflection coefficient with values stored in a memory thereof, which are characteristic of human skin, can only activate the laser source 9 if the values measured by all detectors 63 correspond, within predetermined limits, to the human skin-characteristic values, i.e. if all detectors 63 detect the presence of human skin. As light is reflected by the human skin in a very characteristic way as a function of the wavelength of the light, it is reliably determined by the detectors 63 whether the medium present directly in front of the exit opening 15 actually is human skin. In the example shown, this reliability is substantially further improved in that the detectors 63 measure the reflection coefficient for two different values of the wavelength, i.e. in this example for yellow light having a comparatively short wavelength and for red light having a comparatively long wavelength. As shown in FIG. 4, the light sources 65, 67 and the light sensor 69 are at a predetermined distance d from the surface of the skin 7 only if the skin contact element 21 is in contact with the skin 7 at the location of the relevant detector 63. The amounts of light received by the light sensor depend on the distance between the light sources 65, 67 and the skin 7 and on the distance between the light sensor 69 and the skin 7, and they decrease particularly substantially if the skin contact element 21 is not in contact with the surface of the skin 7, in which case an amount of light from the light sources 65, 67 can escape via the space present between the skin contact element 21 and the skin 7. Therefore, in order to achieve that the values of the reflection coefficient measured by the detectors 63 correspond, within predetermined limits, to the human skin-characteristic values, the exit opening 15 should, on the one hand, actually be covered by human skin and, on the other hand, the skin contact element 21 should be in contact with the surface of the skin 7. It is noted, however, that the reliability with which the detectors 63 can determine the presence of the skin 7 against the skin contact element 21 is smaller than the reliability with which the detectors 43 of the device 1 can determine the presence of the skin against the skin contact element. It is further noted that the invention also comprises modifications of the detectors 63 and of the number and positions thereof, such as the modifications of the detectors 43 described hereinabove.

The above-discussed detectors 43 and detectors 63 of, respectively, the device 1 and the device 1' in accordance with the invention can suitably be used to measure, respectively, the scattering coefficient and/or absorption coefficient of the skin and the reflection coefficient of the skin. It is noted that the invention also comprises embodiments wherein use is made of a detector which is suitable for measuring a different biophysical property by means of which the skin can be characterized, and wherein the comparator of the control unit can suitably be used to compare a value or condition of said property, measured by means of said detector, with a skin-characteristic value or condition of said property. An alternative biophysical property is, for example, the electrical resistance of the skin. This property is less reliable, however, than the above-described properties because the electrical resistance of the skin is influenced by the presence of moisture and additives on the skin. Another conceivable biophysical property is the presence of blood. The flow of blood in the skin is, for example, detectable by means of a laser-doppler measurement, and the resultant measuring signals are very characteristic of human skin. The sensors and processors necessary are more expensive, however, than the light sources and light sensors used in the above-discussed detectors 43 and 63. Other techniques that can suitably be used in a device in accordance with the invention for detecting the presence of skin are skin-imaging techniques, such as optical coherence tomography, confocal microscopy, two-photon microscopy and spectroscopic techniques. These techniques are very reliable, but owing to their complexity they are less suitable for use in devices for the consumer market, and more suitable for use in devices for the professional market.

The above-discussed devices 1 and 1' in accordance with the invention are laser epilation devices. The invention, however, also comprises other types of hair removing devices, wherein hairs are shortened or removed by means of radiation issuing from an exit opening. An example of such a hair removing device is a laser shaver. The operation of such a laser shaver is basically the same as that of the above-discussed laser epilation devices, however, the target position of the laser beam is not in the hair root but in a position on the hair just above the surface of the skin. Another type of hair removing device, to which the invention may, for example, be applicable is a flashlight epilation device. The third example of a device 83 in accordance with the invention, as shown in FIG. 5, is an example of such a flashlight epilation device. The device 83 comprises a housing 85 wherein a frame 87 is arranged. Said frame 87 comprises a chamber 89 wherein a flashlight 91 is arranged as the radiation source, which is a xenon lamp in the example shown. The chamber 89 is filled with a cooling liquid for the flashlight, water being used as the cooling liquid in the example shown. The chamber 89 has a parabolically shaped wall 93, which is coated with a reflective material and hence serves as a reflector or directing element for the light generated by the flash light 91. The chamber 89 is shut off by a transparent plate 95, which, in the example shown, is a long-wave band pass filter. The device 83 further comprises an optical waveguide 97 which opens into an exit opening 99. Around the exit opening 99 there is provided a skin contact element 101 accommodating a number of detectors 103 of a type similar to the above-described detectors 43 or 63. In operation, the flash light 91 generates a series of light pulses having a predetermined pulse duration and intensity, which pulse duration and intensity may vary as a function of time. The light pulses are directed at the exit opening 99 by the wall 93 and reach the exit opening 99 via the transparent plate 95 and the optical waveguide 97. The frequency of the light pulses is such that the light pulses are absorbed, in particular, by the hair roots present in the skin, as a result of which the hair roots are heated and die. For a detailed explanation of the operation of the device 83, which is only briefly described herein, reference is made to EP-A-0 885 629. The flash light 91 can only be activated if all detectors 103 detect the presence of human skin against the skin contact element 101, i.e. if the exit opening 99 is completely covered by human skin.

The devices 1, 1' and 83 discussed hereinabove all are hair removing devices. It is noted that the invention also comprises other types of devices for treating skin by means of radiation. Examples of such devices are devices for the medical treatment of skin by means of radiation, such as by means of laser light, flashlights, or other types of radiation having a comparatively high intensity. Such devices are used, for example, for treating birthmarks, such as naevus pigmentosus and naevus vinosus, present on the skin, psoriasis, or aberrations of blood vessels present in the skin. Other examples of such devices include devices for skin-rejuvenation cures by means of radiation.

It is finally noted that the invention also comprises devices wherein the detector or detectors are arranged in a position that differs from their position in the skin contact element of the device. A position of the detectors in the skin contact element near the exit opening, as in the above-discussed devices 1, 1' and 83, however, generally leads to an optimum protection of the device.

What is claimed is:

1. A device for treating skin by means of radiation, which device comprises a housing, which accommodates a radiation source and which is provided with an exit opening for the radiation, a detector for detecting the presence of skin directly in front of the exit opening, and a control unit capable of activating the radiation source, wherein the detector is configured to measure a value or condition of a biophysical property in an area directly in front of the exit opening, the control unit comprising a comparator for comparing the value or condition of the property, measured by said detector, with a skin-characteristic value or condition of the property and being enabled to activate the radiation source only if the skin-characteristic value or condition is found, wherein the housing comprises a skin contact element in which the exit opening is formed and in which said detector is provided near the exit opening, and wherein the detector is provided with a light sensor and a light source for light of a predetermined wavelength, which light source is arranged next to the light sensor and optically separated at the skin contact element from said light sensor, the skin contact element adapted to be in contact with the skin during operation of the device and the light source and the light sensor configured to be in contact with the skin only if the skin contact element is in contact with the skin, the detector determining a scattering coefficient and/or absorption coefficient by comparing an amount of light measured by the light sensor with an amount of light generated by the light source.

2. A device as claimed in claim 1, wherein the detector is provided with a further light source for light of a further, predetermined wavelength, which light source is also arranged next to the light sensor, optically separated from said light sensor and configured to be in contact with the skin only if the skin contact element is in contact with the skin, the detector determining the scattering coefficient and/or absorption coefficient for both wavelengths by comparing the amounts of light measured by the light sensor with the amounts of light generated by the two light sources.

3. A device as claimed in claim 2, wherein the light source and the further light source are arranged on one side of the light sensor.

4. A device as claimed in claim 1, wherein the light source is a LED, and the light sensor is a photodiode.

5. A device for treating skin comprising:
a housing having an exit opening;
a radiation source accommodated in the housing and positioned to emit radiation through the exit opening;
a control unit capable of controlling the radiation source, the control unit comprising a comparator and a program storage device tangibly embodying a program of instructions executable by the comparator;
a detector enabled to measure a value or condition of a biophysical property of the skin opposite the exit opening and transmit to the control unit a signal corresponding to the measured biophysical property;
the control unit being capable of receiving the signal corresponding to the measured value or condition, and the comparator and the program of instructions being configured to compare the measured value or condition, with a skin-characteristic value or condition of the biophysical property,
the control unit being enabled to activate the radiation source only if the measured value or condition corresponds to the skin-characteristic value or condition of the biophysical property.

6. A device as claimed in claim 5, wherein the housing comprises a skin contact element in which the exit opening is formed and in which said detector is provided near the exit opening.

7. A device as claimed in claim 6, wherein the detector is one of a series of detectors provided in the skin contact element around the exit opening, the series of detectors being enabled to measure the value or condition of the biophysical property of the skin and transmit to the control unit the signal corresponding to the measured biophysical property.

8. A device as claimed in claim 6, wherein the detector is provided with a light sensor and a light source for light of a predetermined wavelength, which light source is arranged next to the light sensor and optically separated from said light sensor, the light source and the light sensor configured to be in contact with the skin only if the skin contact element is in contact with the skin, and the detector tangibly embodying a second program of instructions to determine a scattering coefficient and/or absorption coefficient by comparing an amount of light measured by the light sensor with an amount of light generated by the light source.

9. A device as claimed in claim 8, wherein the detector is provided with a further light source for light of a further, predetermined wavelength, which light source is also arranged next to the light sensor, optically separated from said light sensor and configured to be in contact with the skin only if the skin contact element is in contact with the skin, the detector tangibly embodying a second program of instructions to determine the scattering coefficient and/or absorption coefficient for both wavelengths by comparing the amounts of light measured by the light sensor with the amounts of light generated by the two light sources.

10. A device as claimed in claim 9, wherein the light source and the further light source are arranged on one side of the light sensor.

11. A device as claimed in claim 8, wherein the light source is a LED, and the light sensor is a photodiode.

12. A device as claimed in claim 6, wherein the detector is provided with a light sensor and a light source for light of a predetermined wavelength, which light source is arranged next to the light sensor and optically separated from said light sensor, the light source and the light sensor being situated at a predetermined distance from the skin only if the skin contact element is in contact with the skin, and the detector determining the reflection coefficient by comparing an amount of light measured by the light sensor with an amount of light generated by the light source.

13. A device as claimed in claim 5, wherein the measured value or condition of the biophysical property is a scattering coefficient and/or an absorption coefficient of the skin for light of a predetermined wavelength.

14. A device as claimed in claim 5, wherein the detector tangibly embodies a second program of instructions to determine a reflection coefficient of the skin for light of a predetermined wavelength.

15. A device as claimed in claim 5, wherein the device is a hair removing device, wherein the radiation source comprises a laser source, and the device is further provided with an adjustable laser beam manipulator for positioning a laser beam supplied, in operation, by the laser source in a target position on the skin to be treated.

16. A device as claimed in claim 5, wherein the device is a hair removing device, wherein the radiation source comprises a flashlight for generating light pulses, and the device is further provided with a directing element for directing the light pulses to the exit opening.

17. A device for treating skin comprising:
a housing comprising a skin contact element in which an exit opening is formed;
a radiation source accommodated in the housing and positioned to emit radiation through the exit opening;
a control unit capable of controlling the radiation source, the control unit comprising a comparator and a program storage device tangibly embodying a program of instructions executable by the comparator;

the skin contact element comprising two or more detectors enabled to measure a value or condition of a biophysical property of the skin and transmit to the control unit one or more signals corresponding to the measured biophysical property;

the control unit being capable of receiving the one or more signals corresponding to the measured value or condition, and the comparator and the program of instructions being configured to compare the measured value or condition, with a skin-characteristic value or condition of the biophysical property, the control unit enabled to activate the radiation source only if the measured value or condition corresponds to the skin-characteristic value or condition of the biophysical property.

* * * * *